United States Patent

Bloom et al.

Patent Number: 5,173,510
Date of Patent: Dec. 22, 1992

[54] SIMPLIFIED THIOESTER AND ISOSTERE ANALOGS OF OLEOYL COENZYME A AS HYPOCHOLESTEROLEMIC AGENTS

[75] Inventors: Jonathan D. Bloom, Hartsdale; Minu D. Dutia, West Nyack, both of N.Y.

[73] Assignee: American Cyanamid Company, Stamford, Conn.

[21] Appl. No.: 725,856

[22] Filed: Jul. 3, 1991

Related U.S. Application Data

[62] Division of Ser. No. 501,451, Mar. 29, 1990, Pat. No. 5,053,426.

[51] Int. Cl.$^5$ .................. A61K 31/16; C07C 233/20
[52] U.S. Cl. .................................. 514/616; 564/159; 554/57
[58] Field of Search .............. 260/404, 402.5; 554/37, 554/55, 56, 57; 564/159; 514/616

[56] References Cited

PUBLICATIONS

Bonner et al., J. Biol. Chem., 247(10), 3123-33 (1972).
DeVris, Schaffer, Largis, Dutia, Wang, Bloom and Katucs, A.S; J. Med. Chem, 1986, 29, 1131-1133, Potential Antiatherosclerotic Agents. 5$^1$ An Acyl-CoA:-Cholesterol O-Acyl-Transferase Inhibitor with Hypocholesterolemic Activity.
Bonjers and Bjorkerud-Atherosclerosis 22 (1975) 379-387 Transfer of Cholesterol In Vitro Between Normal Arterial Smooth Muscle Tissue and Serum Lipoproteins of Normo-Lipidemic Rabbits.
Simpson, Burkhart, Arch. Biochem. Biophys., 200, 1, 79-85 (1980) Acyl CoA:Cholesterol Acyl Transferase Activity in Human Placental Microsomes: Inhibition by Progesterone$^1$.
Hashimoto and Dayton, Atherosclerosis, 28 (1977) 447-452 Studies of the Mechanism of Augmented Synthesis of Cholesteryl Ester in Atherosclerotic Rabbit Aortic Microsomes.
Adams et al., Atherosclerosis, 19 (1974) 429-440 Lipid Deposits in Aging Human Arteries, Tendons and Facia.
Bell, Atherosclerosis, 38 (1981) 81-88, The Effect of Local Anesthetics on Arterial Lipid Metabolism.
Bonders and Bjorkerud, Atherosclerosis, 15:273-284 (1972) Arterial Repair dna Atherosclerosis after Mechanical Injury.
Natori, Okazaki, Nakajima, Hirohashi, and Aono, Japan J. Pharmacol. 42, 517-523 (1986) Mechanism of the Inhibition of Cholesterol Absorption by DL-Melinamide: Inhibition of Cholesterol Esterification.
Heider, Pickens and Kelley, Journal of Lipid Research 24:1127-1134, (1983) Role of CoA:cholesterol acyltransfese in cholesterol absorption and its inhibition by 57-118 in the rabbit.
Ross, Go, Heider and Rothblat, Journal of Biological Chem. 259:815-819 (1984) Selective Inhivition of Acyl Coenzyme A:Cholesterol Acyltransferase by Compound 58-03.
Goldstein, Faust, Dygos, Chorvat and Brown, Proc. Natl. Acad. Sci. 75:1877-1881 (1978) Cell Biology, Inhibition of cholesteryl ester formation in human fibroblasts by an analogue of 7-ketocholesterol and by progesterone.
Bell-Exp. Mol. Path. 38,336-345(1983) Effect of Chlorpromazine on Lipid Metabolism in Aortas from Cholesterol-Fed Rabbits and Normal Rats in Vitro:Inhibition of Sterol Esterification and Modification of Phospholipid Synthesis.
Hudson, Day and Marceglia, Expl. Molec. Pathol. 36:156-163 (1982) The Effect of Bezafibrate and Clofibrate on Cholesterol Ester Metabolism in 3T3 Cells and Smooth Muscle Cells in Tissue Culture.
Hudson, Mojourder and Day, Expl. Molec. Pathol, 38: 77-81 (1983) The Effect of Bezafibrate and Clofibrate on Cholesterol Ester Metabolism in Rabbit Peritoneal Macrophages Stimulated with Acetylated Low Density Lipoproteins.

Primary Examiner—Nicky Chan
Attorney, Agent, or Firm—Thomas S. Szatkowski

[57] ABSTRACT

New thioester and ester, amide and ketone isostere analogs of oleoyl coenzyme A, useful as antiatherosclerotic agents, are provided. The compounds have the formula:

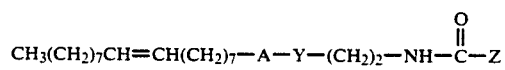

wherein A is selected from the group consisting of

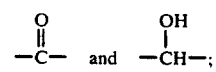

Y is selected from the group consisting of —S—, —O—, —NH— and (—CH$_2$—)$_n$ wherein n=1 to 4; and Z is selected from the group consisting of alkyl (C$_1$-C$_6$),

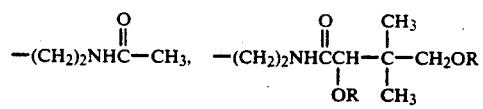

wherein R=Hydrogen, C$_1$-C$_4$ alkyl or C$_1$-C$_4$ acyl, and

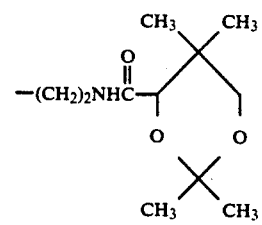

7 Claims, No Drawings

SIMPLIFIED THIOESTER AND ISOSTERE ANALOGS OF OLEOYL COENZYME A AS HYPOCHOLESTEROLEMIC AGENTS

This is a divisional of co-pending application Ser. No. 07/501,451 filed on Mar. 29, 1990 now U.S. Pat. No. 5,053,426.

BACKGROUND OF THE INVENTION

1. Field of the Invention

The invention relates to novel simplified thioester and isostere analogs of oleoyl coenzyme A which are useful as antiatherosclerotic agents capable of ameliorating atherosclerosis by counteracting the formation or development of atheromatous lesions in the arterial wall of mammals. The invention also relates to the chemical synthesis of the novel compounds disclosed herein. In addition, the invention pertains to novel pharmaceutical compositions for the utilization of these compounds in the treatment of disease in mammals. Further, the invention contemplates methods for treating atherosclerosis in a manner designed to prevent, arrest, or reverse the course of the disease.

2. Description of the Prior Art

Atherosclerosis is a form of arteriosclerosis characterized by lipid accumulation in and thickening of the arterial walls of both medium- and large-sized arteries. Arterial walls are thereby weakened, and the elasticity and effective internal size of the artery is decreased. Atherosclerosis is the most common cause of ischemic heart disease and is of great medical importance since the occlusion of medium- and large-sized arteries diminishes the supply of blood to vital organs such as the heart muscles and the brain. The sequelae to atherosclerosis include ischemic heart disease, heart failure, life-threatening arrythmias, senility, and stroke.

The fact that cholesterol is a major component of atherosclerotic lesions or plaques has been known for more than 100 years. Various researchers have studied the role of cholesterol in lesion formation and development and also, more importantly, whether lesion formation can be prevented or lesion development arrested or reversed Atheromatous lesions have now been shown [Adams, et al., Atherosclerosis, 13: 429 (1974)] to contain a greater quantity of esterified as opposed to unesterified cholesterol than the surrounding undiseased arterial wall. The intracellular esterification of cholesterol with fatty acids via the transesterification reaction of cholesterol and fatty acyl CoA derivatives (primarily oleoyl CoA) is catalyzed by the enzyme fatty acyl CoA:cholesterol acyl transferase or ACAT, and the accumulation and storage of cholesterol esters in the arterial wall is associated with increased activity of this enzyme [Hashimoto and Dayton, Atherosclerosis, 28: 447 (1977)]. In addition, cholesterol esters are removed from cells at a slower rate than unesterified cholesterol [Bondjers and Bjorkerud, Atherosclerosis, 15: 273 (1972) and 22: 379 (1975)]. Thus, inhibition of the ACAT enzyme would diminish the rate of cholesterol esterification, decrease the accumulation and storage of cholesterol esters in the arterial wall, and prevent or inhibit the formation and development of atheromatous lesions.

A number of compounds are reported to be inhibitors of ACAT—catalyzed cholesterol esterification. These include the local anesthetics lidocaine, tetracaine, benzocaine and dibucaine [Bell, Atherosclerosis, 1981, 38, 81], the tranquilizer chlorpromazine [Bell, Exp. Mol. Pathol, 1983, 38, 336], the hypolipidemics clofibrate and benzafibrate [Hudson, Day and Marceglia, Expl. Molec. Pathol, 1982, 36, 156; Hudson, Mojuorder and Day, Expl. Molec. Pathol, 1983, 38, 77], progesterone [Goldstein, Faust, Dygos, Chorvat, and Brown, Proc. Natl. Acad. Sci., 1978, 75, 1877 and Simpson, Burkhart, Arch. Biochem Biophys, 1980, 200, 79], melinamide [Natori, Okazaki, Nakajima, Hirohashi, and Aono, Japan J. Pharmacol 1986, 10, 403], ethyl ester of (z)-N-(1-oxo-9- octadecenyl)-D,L-tryptophan [Heider, Pickens and Kelly, J. Lipid. Res., 1983, 24, 1127], (3-decyldimethyl silyl)-N-[Z-(4-methylphenyl)-1-phenethyl] propionamide) [Ross, Go, Heider and Rothblat, J. Biol. Chem, 1984, 259, 815] and N,-2,4-difluorophenyl-N-n-heptyl-N-(4-neopentyl) benzyl urea [DeVries, Schaffer, Langis, Dutia, Wang, Bloom and Katucs, A.S.J. Med. Chem, 1986, 29, 1131].

SUMMARY OF THE INVENTION

This invention relates to new simplified thioester and ester, amide and ketone isostere analogs of oleoyl coenzyme A having the formula:

$$CH_3(CH_2)_7CH=CH(CH_2)_7-A-Y-(CH_2)_2-NH-\overset{O}{\underset{\parallel}{C}}-Z$$

wherein A is selected from the group consisting of

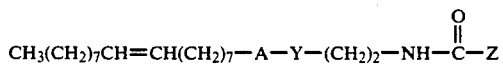

Y is selected from the group consisting of —S—, —O—, —NH— and —(CH$_2$)$_n$-wherein n=1 to 4; and Z is selected from the group consisting of alkyl (C$_1$-C$_6$),

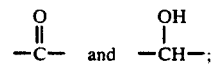

and

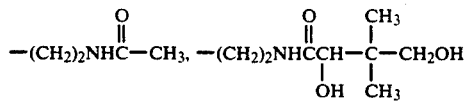

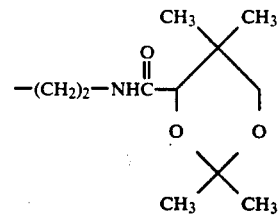

The invention also relates to a method of treating atherosclerosis in mammals which comprises administering to said mammal an effective amount of a compound as recited above.

The invention also relates to a method of reducing the cholesterol content of the arterial walls of mammals which comprises administering to said mammal an effective amount of a compound as recited above.

The invention also relates to a method of treating hyperlipidemia in mammals which comprises administering to said mammal an effective amount of a compound as recited above.

The invention further relates to a method of inhibiting atherosclerotic lesion development in mammals which comprises administering to said mammal an effective amount of a compound as recited above.

The invention still further relates to pharmaceutical compositions which comprise an effective antiatherosclerotic amount of a compound as recited above in association with a pharmaceutically acceptable carrier.

Finally, the invention relates to processes for preparing compounds as recited above.

DESCRIPTION OF THE PREFERRED EMBODIMENTS

-continued
Scheme I

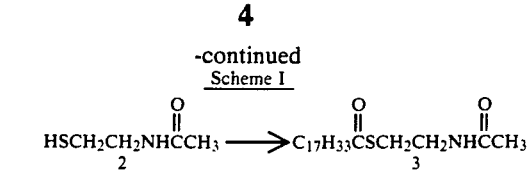

According to Scheme I, oleoyl chloride 1 is reacted with N-acetylcysteamine 2 in tetrahydrofuran giving the thioester product S-[2-(acetylamino)ethyl]-9(Z)-octadecenethioic acid 3.

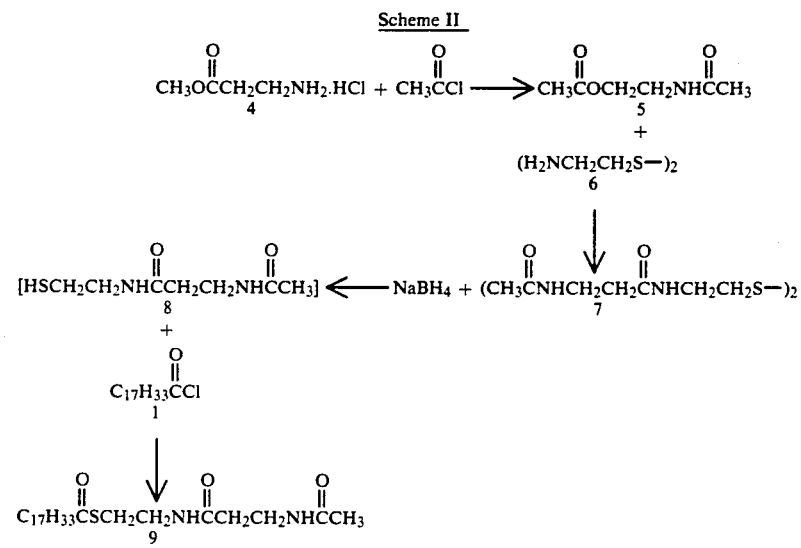

The compounds of this invention may be prepared by one or more of the following reaction schemes. Synthesis of the thioester series is described in Schemes I, II and III.

Scheme I

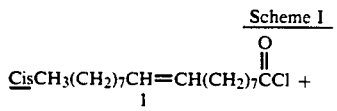

According to scheme II, β-alanine methyl ester hydrochloride 4 is reacted with acetyl chloride giving N-acetyl-β-alanine methyl ester 5 which is reacted with disulfide cystamine 6 upon heating neat at 80° C. giving the tetraamide disulfide product N, N-(Dithiodi-2,1-ethanediyl bis [3-(acetylamino) propanamide 7. Reductive cleavage of the disulfide bond of 7 with sodium borohydride in methanol gives the unstable thiol 8 which is reacted in situ with an excess of oleoyl chloride 1, giving the thioester product S-[2-[[3-(acetylamino)-1-oxopropyl]amino]ethyl]-9(Z)-octadecenethioate 9.

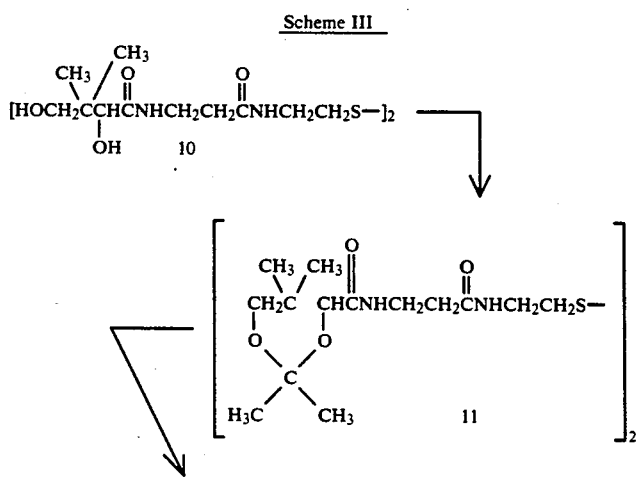

Scheme III

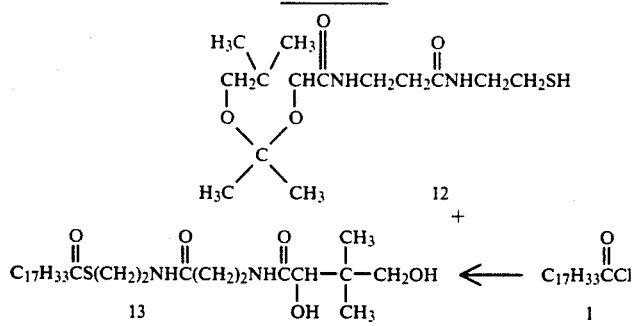

According to scheme III, D-pantethine 10 is reacted with 2,2-dimethoxypropane and trifluoroacetic acid in acetone, giving pantethine acetonide 11 which is reacted with sodium borohydride, giving the crude thiol 12 which is immediately reacted with oleoyl chloride giving the thioester product S-[2-[[1-oxo-3-[[2,2,5,5-tetramethyl-1,3-dioxan-4-yl) carbonyl]amino]propyl]amino]ethyl]-9(z)-octadecenethioate. The acetonide is then removed with trifluoroacetic acid in methanol, giving the thioester product S-[2-[[3-[(2,4-dihydroxy-3,3-dimethyl-1-oxobutyl]amino]-1-oxopropyl]amino]ethyl]-9(Z)-octadecenethioate acid 13.

Synthesis of the ester isostere series is described in schemes IV, V and VI.

Scheme IV

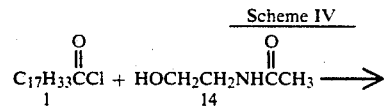

-continued
Scheme IV

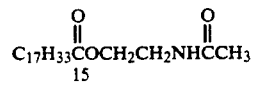

According to scheme IV, oleoyl chloride 1 is treated with N-acetylethanolamine 14 in tetrahydrofuran, giving the ester isostere product 2-(acetylamino)-9(Z)-octadecenoate 15.

Scheme V

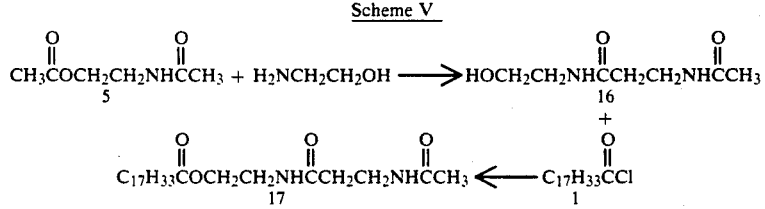

According to scheme V, N-acetyl-β-alanine methyl ester 5 is reacted with ethanolamine neat at 85° C., giving 3-(acetylamino)-N-(2-hydroxyethyl)propanamide 16 which is reacted with oleoyl chloride 1, giving the ester isostere product 2-[[3-(acetylamino)-1-oxopropyl]amino]ethyl-9(Z)-octadecenoate 17.

Scheme VI

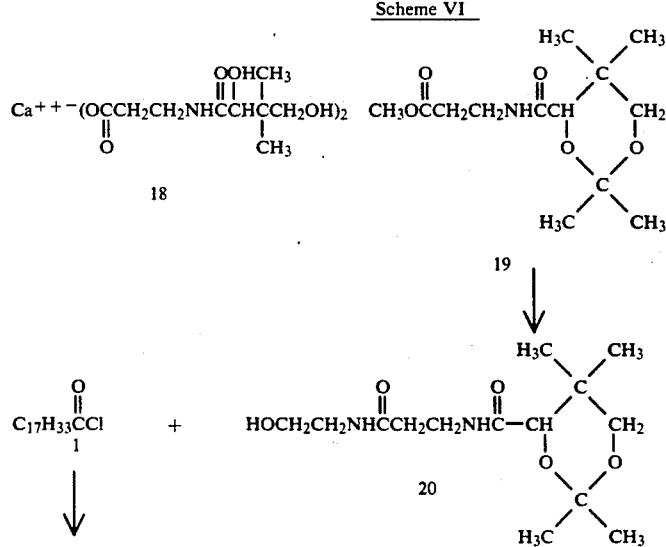

Scheme VI

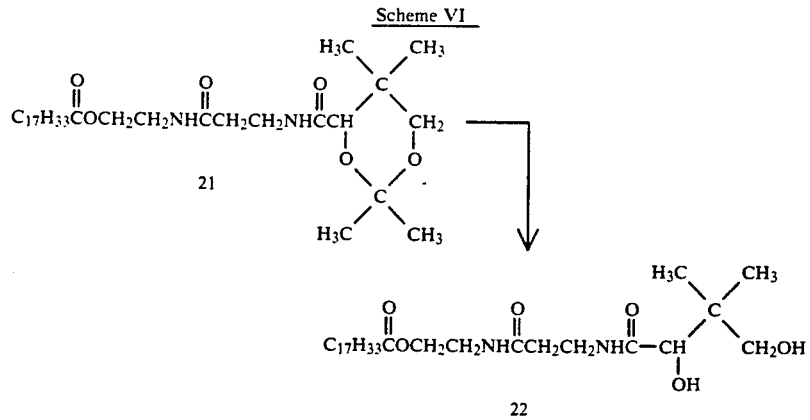

According to scheme VI, calcium pantothenate 18 is slurried in acetone/2,2-dimethoxypropane and reacted with trifluoroacetic acid dropwise followed by treatment with methyl iodide and potassium carbonate in acetonitrile giving N-[(2,2,5,5-tetramethyl-1,3-dioxan-4-yl) carbonyl]-β-lanine, methyl ester 19 which is heated with one equivalent of ethanolamine to produce the alcohol N-[3-[(2-hydroxyethyl) amino-3-oxopropyl]-2,2,5,5-tetramethyl-1,3-dioxane-4-carboxamide 20 which is reacted with oleoyl chloride giving the protected pantothenate derivative 2-[[3-[[2,2,5,5-tetramethyl-1,3,dioxan-4-yl)carbonyl]amino-1-oxopropyl]amino]ethyl-9(z)-octadecenoate 21 followed by cleavage with trifluoroacetic acid in methanol, giving the ester isostere product 2-[[3-[(2,4-dihydroxy-3,3-dimethyl-1-oxobutyl)amino]-1-oxopropyl]amino]ethyl-9(Z)octadecenoate 22.

Synthesis of the amide isostere series is described in schemes VII, VIII, and IX.

Scheme VII

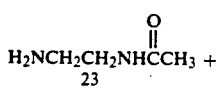

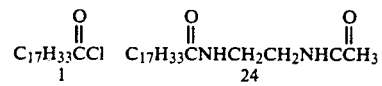

According to scheme VII, N-acetylethylenediamine 23 is reacted with oleoyl chloride 1, giving the amide isostere product N-[2-(acetylamino)ethyl]-9(Z)octadeceneamide 24.

Scheme VIII

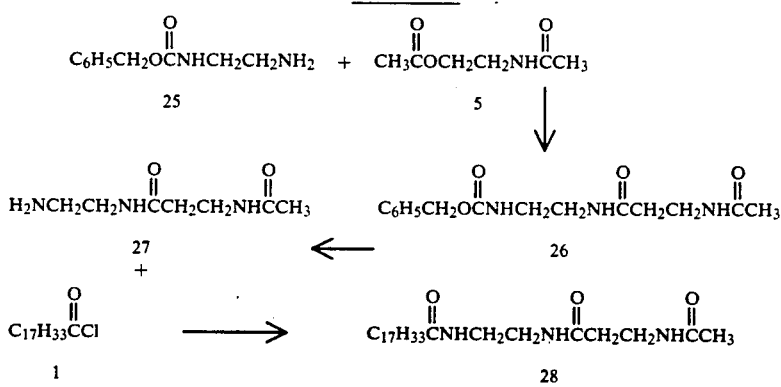

According to scheme VIII, ethylenediamine is first treated with an excess of benzyl chloroformate followed by mono-hydrolysis using hydrochloric acid in glacial acetic acid giving N-carboxybenzylethylenediamine 25 which is treated with N-acetyl-β-alanine methyl ester 5, giving the protected carbamate [2-[[-(acetylamino)-1-oxopropyl]amino]ethyl]carbamic acid, phenylmethyl ester 26 which is deprotected using palladium on carbon in refluxing ethanol/cyclohexane, giving amine 3-(acetylamino)-N-(2-aminoethyl)propanamide 27. Amine 27 is reacted with oleoyl chloride 1 to give the amide isostere product N-[2-[[3-(acetylamino)-1-oxopropyl]amino]ethyl]-9(Z)-octadecenamide 28.

Scheme IX

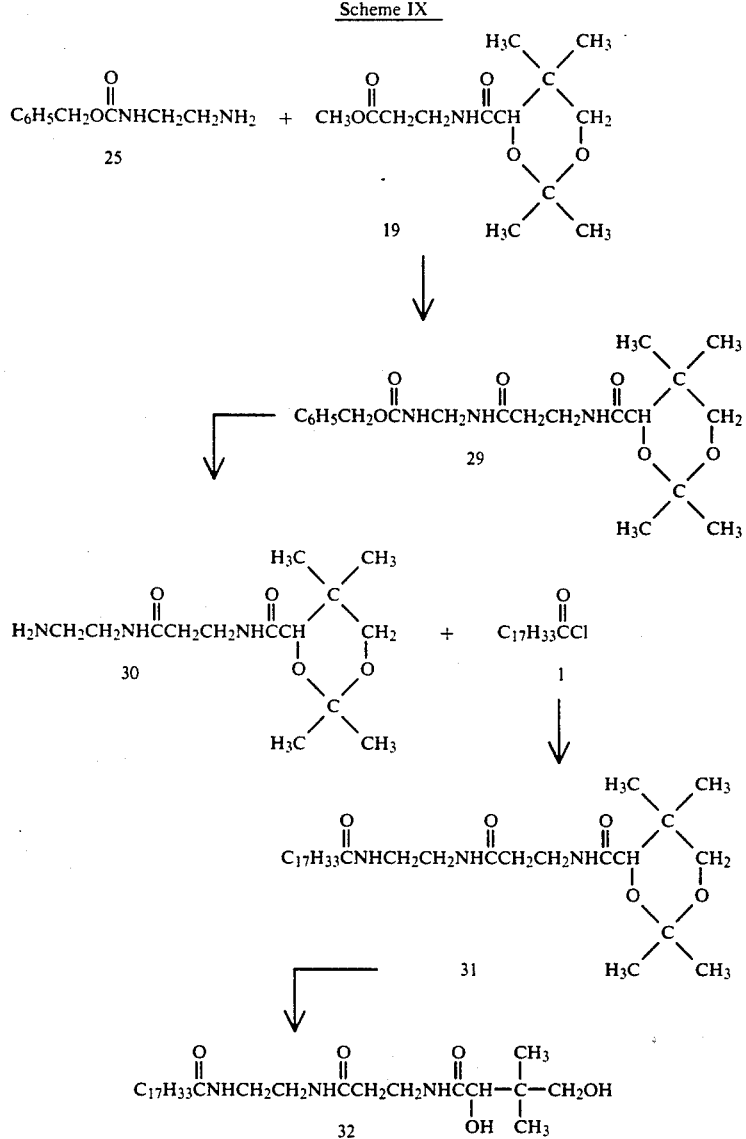

According to scheme IX, treatment of ester 19 with N-carboxybenzylethylenediamine 25 gives the protected carbamate [2-[[1-oxo-3-[[(2,2,5,5-tetramethyl-1,3-dioxan-4-yl) carbonyl] amino]propyl]amino]ethylcarbamic acid phenylmethyl ester 29 which is hydrogenolyzed to give the amine N-[3-[(2-aminoethyl)amino-3-oxoipropyl]-2,2,5,5-tetramethyl-1,3-dioxane-4-carboxamide 30. Treatment of 30 with oleoyl chloride I, gives 2,2,5,5-tetramethyl-N-[3-oxo-3-[[2-[(1-oxo-9(Z)-octadecenyl) amino]ethyl]amino]propyl]-1,3-dioxane-4-carboxamide 31 which may be cleaved by acid catalysis to give the amide isostere product N-[2-[[3-[(2,4-dihydroxy-3,3-dimethyl-1-oxobutyl)amino]-1-oxopropyl]amino]ethyl]-9(Z)octadecenamide 32.

Synthesis of the ketone isostere series is described in schemes X, XI and XII.

Scheme X

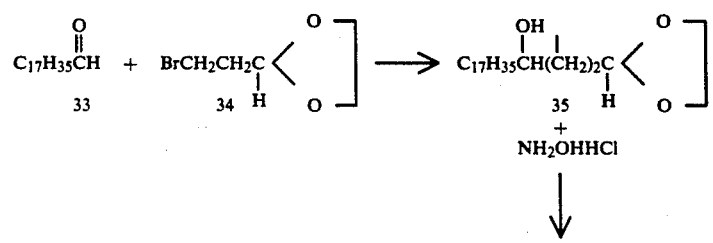

Scheme X

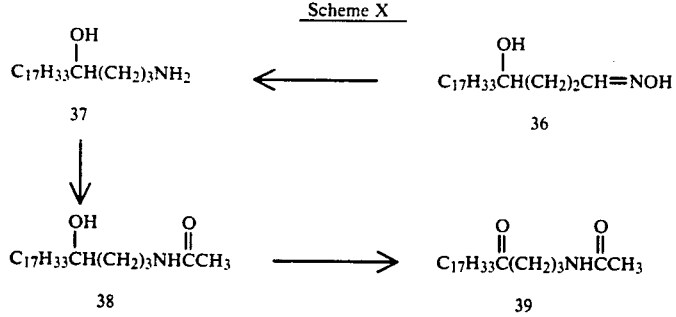

According to scheme X, olealdehyde 33, produced from the reaction of oleyl alcohol and pyridinium chlorochromate, is reacted with the Gignard reagent derived from 2-(2-bromoethyl)-1,3-dioxolane 34 in tetrahydrofuran, giving α-8(Z)-heptadecenyl-1,3-dioxolane-2-propanol 35 which is treated with hydroxylamine hydrochloride to produce 4-hydroxy-12(Z)-eicosenaloxime 36. Reaction of 36 with lithium aluminum hydride gives 1-amino-12(Z)-eicosen-4-ol 37, which is reacted with acetic anhydride to produce N-(4-hydroxy-12(Z)-eicosenyl)acetamide 38, which may be reacted with pyridinium chlorochromate to give the ketone product N-(4-oxo-12(Z)-eicosenyl)acetamide 39.

Scheme XI

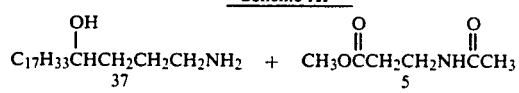

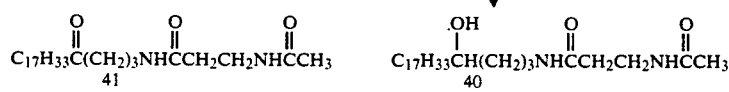

According to scheme XI, 1-amino-12(Z)-eicosen-4-ol 37 and N-acetyl-β-alanine methyl ester are heated at 80° C. under an inert atmosphere giving 3-(acetylamino)-N-(4-hydroxy-12(Z)-heneicosenyl) propanamide 40 which may then be reacted with pyridinium chlorochromate giving the ketone product 3-(acetylamino)-N-(4-oxo-12(Z)-heneicosenyl) propanamide 41.

Scheme XII

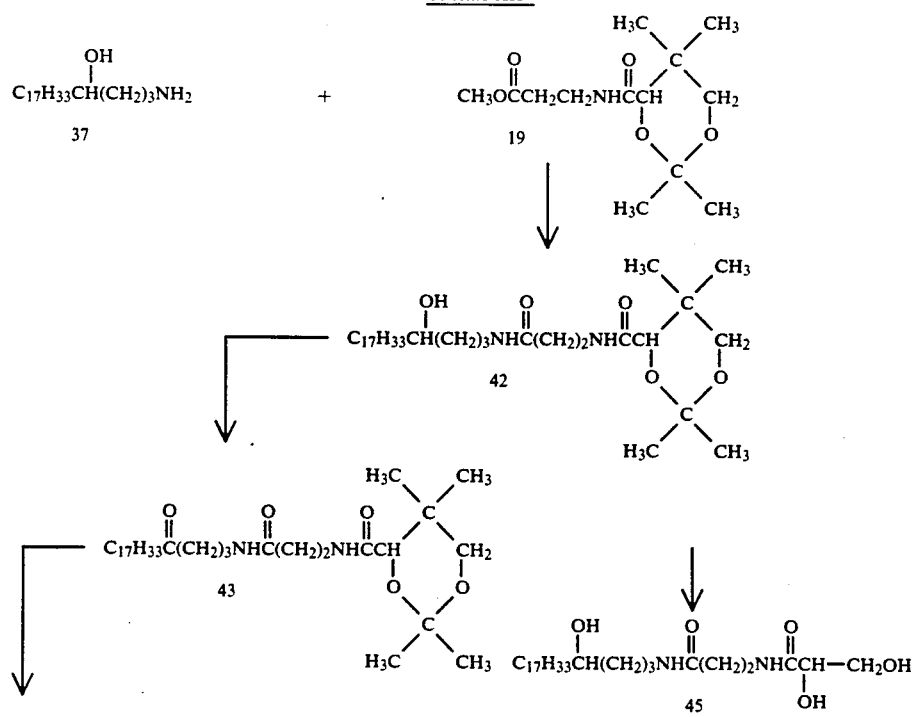

Scheme XII
-continued

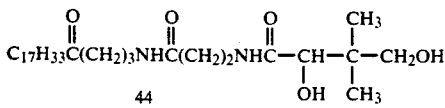

According to scheme XII, 1-amino-12(Z)-eicosen-4-ol 37 and N-[(2,2,5,5-tetramethyl-1,3-dioxan-4-yl) carbonyl]-β-alanine, methyl ester 19 are reacted at 80° C. under an inert atmosphere, giving N-[3-[(4-hydroxy-12(Z)-heneicosenyl)amino]-3-oxopropyl]-2,2,5,5-tetramethyl-1,3-dioxane-4-carboxamide 42, which is treated with pyridinium chlorochromate to produce 2,2,5,5-tetramethyl-N-[3-oxo-3-[(4-oxo-12(Z)-heneicosenyl)amino]propyl]-1,3-dioxane-4-carboxamide 43 which is then deprotected with trifluoroacetic acid in methanol, giving the ketone product 2,4-dihydroxy-2,2-dimethyl-N-[ 3-oxo-3-[(4-oxo-12(Z)-heneicosenyl)amino]propyl]butanamide 44. The acetonide is removed from 42 with trifluoroacetic acid in methanol giving 2,4-dihydroxy-N-[3-[(4-hydroxy-12(z)-heneicosyl)amino]-3-oxopropyl]-3,3-dimethyl butanamide, 45.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

Oleoyl chloride, 1

A 1.0 g portion of oleic acid was dissolved in 10 ml of hexane. A 2.0 ml portion of oxalyl chloride was added and this mixture was stirred under dry conditions for 1.5 hours, then evaporated in vacuo, giving the desired compound as a colorless oil.

EXAMPLE 2

N-acetylcysteamine. 2

A 1.0 g portion of cysteamine was slurried with 25 ml of tetrahydrofuran. A solution of 1.32 g of acetic anhydride in 10 ml of tetrahydrofuran was added over 2 minutes. This reaction was stirred for 15 hours, then poured into water and extracted twice with ether. The ether extracts were combined, dried and evaporated, giving 0.62 g of the desired compound as a colorless oil.

EXAMPLE 3

S-[2-(Acetylamino)ethyl-9(Z)-octadecenethioic acid, 3

A 0.25 g portion of N-acetylcysteamine was dissolved in 5 ml of tetrahydrofuran and added to a solution of 0.63 g of oleyl chloride in 5 ml of tetrahydrofuran. A 1 ml portion of triethylamine and 20 mg of 4-dimethylaminopyridine was added, the white slurry stirred for 15 minutes, then poured into brine and extracted twice with ether. The extracts were combined, washed with 2N hydrochloric acid, then brine, dried and concentrated. The 0.7 g of white waxy residue was purified by flash chromatography [hexane:ethyl acetate (2:1)] giving the desired product as 0.41 g of white solid, mp 36°–38° C.

EXAMPLE 4

N-Acetyl-β-alanine methyl ester, 5

A 10.0 g portion of β-alanine methyl ester hydrochloride was slurried in 200 ml of dichloromethane. A 20 ml portion of acetyl chloride and 20 g of anhydrous potassium carbonate were added and the mixture was stirred vigorously for 48 hours. The mixture was poured into 400 ml of ether, 20 g of fresh anhydrous potassium carbonate added and the solids allowed to settle for 15 minutes. Suction filtration through celite and concentration gave an oil. This oil was concentrated four times from 50 ml portions of toluene, giving 4.73 g of the desired compound as a pale yellow oil.

EXAMPLE 5

N,N'-(Dithiodi-2,1-ethanediyl)bis[3-(acetylamino)propanamide 7

A 0.95 g portion of disulfide cystamine and 1.81 g of N-acetyl-β-alanine methyl ester were heated together at 80° C. under argon for 4 hours. The resulting solid was broken up, methanol added and 1.47 g of white powder recovered by filtration. This powder was recrystallized from glacial acetic acid/acetonitrile, giving the desired compound, mp 210°–212° C.

EXAMPLE 6

S-[2 [[3-(Acetylamino)-1-oxopropyl]amino]ethyl]-9(Z)-octadecenethioate, 9

A 1.0 g portion of N,N'-(dithiodi-2,1-ethanediyl)-bis[3-(acetylamino)propanamide was slurred in 5 ml of absolute methanol A 100 mg portion of sodium borohydride was added. The resulting solution was stirred for 20 minutes and then added to a solution of 318 mg of oleoyl chloride in 5 ml of tetrahydrofuran. A 1.0 ml portion of triethylamine was added, the mixture was stirred for 15 minutes, then poured into aqueous ammonium chloride and extracted twice with ether. The extracts were combined, washed with brine, dried and concentrated giving a whitish film. This film was purified by flash chromatography eluting with ethyl acetate:hexane (4:1), then ethyl acetate:methanol (100:1), giving 0.34 g of the desired product as a white powder, mp 125°–127° C.

EXAMPLE 7

Pantethine acetonide, 11

A mixture of 1.0 g of D-pantethine, 5 ml of 2,2-dimethoxypropane, 5 drops of trifluoroacetic acid and 5 ml of acetone was stirred for 2 days and then evaporated. The resulting white foam was purified by flash chromatography [dichloromethane:methanol (10:1)], giving 1.0 g of the desired compound as a white hygroscopic foam.

EXAMPLE 8

Crude Thiol, 12

A 0.96 g portion of pantethine acetonide was dissolved in 50 ml of absolute methanol. A 1.0 g portion of sodium borohydride was added. After the initial vigorous reaction subsided, the mixture was stirred under argon for 2 hours, then poured into water and neutralized with 2N sulfuric acid. The mixture was salted and extracted three times with ethyl acetate. The extracts were combined, washed with brine, dried and evaporated. The residue was dried in vacuo giving the desired compound as a foam.

EXAMPLE 9

S-[2-[[1-Oxo-3-[[(2,2,5,5-tetramethyl-1,3-dioxan-4-yl)carbonylamino]amino]ethyl]-9(Z)-octadecenethioate The crude thiol prepared in Example 8 as a foam was dissolved in 50 ml of dry tetrahydrofuran and treated with 5 ml of triethylamine, followed by a solution of 1.0 g of oleyl chloride in 25 ml of tetrahydrofuran. This mixture was stirred for 1 hour, then poured into salty water and extracted twice with ethyl acetate. The extracts were combined, washed with brine, dried and evaporated, giving a green waxy solid. This solid was purified by flash chromatography, eluting with ethyl acetate:hexane (1:1, then 3:2), giving 0.66 g of the desired compound as a colorless syrup.

EXAMPLE 10

S-2-[[3-[(2,4-Dihydroxy-3,3-dimethyl-1-oxobutyl)amino]-1-oxopropyl]amino]ethyl]-9(Z)-octadecenethioic acid, 10

A 0.5 g portion of S-[2-[[1-oxo-3-[[(2,2,5,5-tetramethyl-1,3-dioxan-4-yl)carbonyl]amino]propyl] amino]ethyl]-9(Z)-octadecenethioate was dissolved in 50 ml of methanol and 1 ml of trifluoroacetic acid added. The colorless solution was allowed to stand overnight and was then evaporated. The resulting gum was purified by flash chromatography, eluting with dichloromethane:methanol (20 1), giving 0.32 g of the desired product as a colorless syrupy gum.

EXAMPLE 11

2-(Acetylamino)-9(Z)-octadecenoate, 15

To a solution of 1 0 g of oleoyl chloride in 10 ml of tetrahydrofuran was added a solution of 0.42 g of N-acetyl ethanolamine and 2 ml of triethylamine in 15 ml of tetrahydrofuran. This mixture was stirred for 12 hours, then poured into water and extracted with ether. The ether extract was washed with 2N hydrochloric acid and brine, then dried and evaporated. The residual yellow oil was purified by flash chromatography, eluting with hexane:ethyl acetate (2:1), giving 0.32 g of the desired product as a pale yellow oil.

EXAMPLE 12

3-(Acetylamino)-N-(2-hydroxyethyl)propanamide, 16

A mixture of 0.42 g of ethanolamine and 1.0 g of N-acetyl-$\beta$-alanine methyl ester was heated at 85° C. for 4 hours. The resulting yellow oil solidified upon cooling and was crystallized from acetonitrile, giving 0.75 g of the desired compound as a white solid, mp 122°–125° C.

EXAMPLE 13

2-[[3-(Acetylamino)-1-oxopropyl]amino]ethyl-9(Z)-octadecenoate 17

A 0.5 g portion of 3-(acetylamino)-N-(2-hydroxyethyl)propanamide, 0.86 g of oleoyl chloride and 1 ml of triethylamine were reacted as described in Example 11. Crystallization of the crude yellow solid from ethyl acetate/toluene gave 0.23 g of the desired product as a white powder. Further purification by flash chromatography, eluting with dichloromethane: methanol (30:1) gave an analytical sample with a melting point of 110°–113° C.

EXAMPLE 14

N-[(2,2,5,5-Tetramethyl-1,3-dioxan-4-yl)carbonyl]-$\beta$-alanine methyl ester, 19

A 5.0 g portion of calcium pantothenate was slurred in 100 ml of acetone:2,2-dimethoxypropane (1:1). Trifluoroacetic acid (3.0 ml) was added until solution was complete and stirring was continued overnight. A 10 g portion of potassium carbonate was added, this mixture stirred vigorously for 10 minutes and then concentrated to a gummy solid. A 100 ml portion of acetonitrile and 10 ml of methyl iodide were added to the solid. This mixture was stirred for 1 day, then poured into water and extracted twice with ethyl acetate. The extracts were combined, dried and concentrated, giving 4.8 g of the desired compound as a yellow oil.

EXAMPLE 15

N-[3-[(2-Hydroxyethyl)amino-3-oxopropyl]-2,2,5,5-tetramethyl-1,3-dioxane-4-carboxamide, 20

A 0.34 g portion of ethanolamine and 1.54 g of N-[(2,2,5,5-tetramethyl-1,3-dioxan-4-yl)carbonyl]-$\beta$-alanine, methyl ester were heated together at 70° C. overnight under argon. The resulting solid was recrystallized from acetonitrile, giving 1.35 g of the desired compound as an off-white solid.

EXAMPLE 16

2-[[3-[[(2,2,5,5-Tetramethyl-1,3-dioxan-4-yl)carbonyl]amino]-1-oxopropyl]amino]ethyl-9(Z)-octadecenoate, 21

A 0.5 g portion of N-[3-[(2-hydroxyethyl)amino-3-oxopropyl]-2,2,5,5-tetramethyl-1,3-dioxane-4-carboxamide and 0.5 g of oleoyl chloride was treated as described in Example 11. The resulting crude yellow oil was purified by flash chromatography, eluting with hexane:ethyl acetate (1:1, then 1:2), giving 0.32 g of the desired compound as a colorless syrup.

EXAMPLE 17

2-[[3-(2,4-Dihydroxy-3,3-dimethyl-1-oxobutyl)amino]-1-oxopropyl]amino]ethyl-9(Z)-octadecenoate 22

A 0.25 g portion of 2-[[3-[[(2,2,5,5-tetramethyl-1,3-dioxan-4-yl)carbonyl]amino]-1-oxopropyl]amino]ethyl-9(Z)-octadecenoate was treated as described in Example 10. The resulting crude colorless syrup was purified by flash chromatography, eluting with dichloromethane:methanol (20:1), giving 0.16 g of the desired product as a colorless gum.

EXAMPLE 18

N-[2-(Acetylamino)ethyl]-9(Z)-octadecenamide, 24

A 1.0 g portion of oleoyl chloride, 0.41 g of N-acetylethylenediamine and 2 ml of triethylamine were reacted as described in Example 11. The crude product was dissolved in dichloromethane, filtered through hydrous magnesium silicate and the filtrate evaporated, giving 0.86 g of the desired product as a white powder which was further purified by flash chromatography, eluting with ethyl acetate:hexane (1:1). The product had a melting point of 137°–141° C.

EXAMPLE 19

N-Carboxybenzylethylenediamine, 25

To a solution of 25 ml of ethylenediamine in water was added at the same time, from two different addition funnels, over a period of four hours, 161 ml of benzyl chloroformate and 740 ml of 1N sodium hydroxide. This mixture was stirred for 30 minutes, then the aqueous solution was decanted from the gummy residue. The residue was washed with water, triturated with petroleum ether, collected, washed with water and petroleum ether and dried at 50° C. under high vacuum, giving 112.0 g of solid.

A mixture of the 112.0 g of solid, 66 ml of concentrated hydrochloric acid and 500 ml of glacial acetic acid was refluxed for 50 minutes, then cooled overnight. The mixture was filtered, the filtrate diluted with 4 liters of ether and allowed to stand for 3.5 hours. The solid was collected, washed with ether and crystallized from 600 ml of hot ethanol. These crystals were collected, washed with ethanol and ether and dried, giving 51 g of N-carboxybenzylethylenediamine hydrochloride, mp 160°–164° C.

A suspension of 19.5 g of the above hydrochloride in 300 ml of water was basified to pH 14 with sodium hydroxide solution. The mixture was stirred for 10 minutes, filtered and the filtrate extracted with three 100 ml portions of dichloromethane. The extracts were combined, washed with brine, dried, filtered and evaporated to dryness, giving 14.5 g of the desired compound as the free base.

EXAMPLE 20

2-[[3-(Acetylamino)-1-oxopropyl]amino]ethyl]carbamic acid, phenylmethyl ester 26

A mixture of 2.09 g of N-carboxybenzylethylenediamine and 1.55 g of N-acetyl-$\beta$-alanine, methyl ester was heated at 70° C. under argon for 15 hours. The residue was dissolved in 60 ml of hot acetonitrile, then cooled and the solid collected, giving 1.9 g of the desired compound as a white solid, mp 180°–182° C.

EXAMPLE 21

3-(Acetylamino)-N-(2-aminoethyl)propanamide 27

A mixture of 1.3 g of [2-[[3-(acetylamino)-1-oxopropyl]amino]ethyl]carbamic acid, phenylmethyl ester, 25 ml of cyclohexane and 180 mg of 10% palladium on carbon in 50 ml of ethanol was heated for 15 hours under argon and then stirred at room temperature for 12 hours. The mixture was filtered through a pad of celite and washed with methanol. The combined filtrate and wash was evaporated, giving 670 mg of the desired compound as a white solid.

EXAMPLE 22

N-[2-[[3-(Acetylamino)-1-oxopropyl]amino]ethyl]-9(Z)-octadecenamide, 28

To a suspension of 300 mg of 3-(acetylamino)-N-(2-aminoethyl)propanamide in 80 ml of tetrahydrofuran containing 1 ml of triethylamine was added dropwise a solution of 521 mg of oleoyl chloride in 10 ml of tetrahydrofuran. The mixture was stirred for 15 hours and then poured into water. The addition of ethyl acetate produced a solid which was collected and recrystallized from methanol, giving 300 mg of the desired product as a white powder, mp 186°–189° C.

EXAMPLE 23

[2-[[1-Oxo-3-[[(2,2,5,5-tetramethyl 1,3-dioxan-4-yl)carbonyl]amino]propyl]amino]ethylcarbamic acid phenylmethyl ester, 29

A mixture of 323 mg of N-[(2,2,5,5-tetramethyl-1,3-dioxan-4-yl)carbonyl]-$\beta$-alanine, methyl ester and 230 mg of N-carboxybenzylethylenediamine was heated at 85° C. under argon for 21 hours. Flash chromatography of the resulting oil, eluting with dichloromethane, followed by dichloromethane:methanol (20:1) gave 205 mg of the desired compound as a beige foam.

EXAMPLE 24

N-[3-[(2-Aminoethyl)amino]-3-oxopropyl]-2,2,5,5-tetramethyl-1,3-dioxane-4-carboxamide, 30

A 150 mg portion of [2-[[1-oxo-3-[[(2,2,5,5-tetramethyl-1,3-dioxan-4-yl)carbonyl]amino]propyl]amino]ethylcarbamic acid phenylmethyl ester was treated as described in Example 21, giving 58 mg of the desired compound as a light brown oil.

EXAMPLE 25

2,2,5,5-Tetramethyl-N-3-oxo-3-[2-[(1-oxo-9(Z)octadecenyl)amino]ethyl]amino]propyl]-1,3-dioxane-4-carboxamide, 31

A mixture of 1.1 g of N-[3-[(2-aminoethyl)amino]-3-oxopropyl]-2,2,5,5-tetramethyl-1,3-dioxane-4-carboxamide, 1.1 g of oleoyl chloride and 3 ml of triethylamine in 100 ml of tetrahydrofuran was reacted as described in Example 11. The crude product was purified by flash chromatography, eluting with dichloromethane:methanol (50:1, then 20:1), giving 400 mg of the desired product as a white solid, mp 110°–112° C.

EXAMPLE 26

N-[2-[[3[(2,4-Dihydroxy-3,3-dimethyl-1-ocobutyl)amino]-1-oxopropyl]amino]ethyl]-9(Z)-octadecenamide, 32

A 220 mg portion of 2,2,5,5-tetramethyl-N-[3-oxo-3-[[2-[(1-oxo-9(Z)-octadecenyl)amino]ethyl]amino]propy-1]-1,3-dioxane-4-carboxamide was treated as described in Example 10. The crude product was purified by flash chromatography, eluting with dichloromethane:methanol (20:1), giving 140 mg of the desired product as a white waxy solid, mp 88°–90° C.

EXAMPLE 27

Olealdehyde, 33

An 18 g portion of pyridinium chlorochromate was slurried in 200 ml of dichloromethane. A solution of 15 g of oleyl alcohol in 200 ml of dichloromethane was added. This mixture was stirred for 4 hours, then poured into ether and filtered through hydrous magnesium silicate. The filtrate was evaporated, giving 13.42 g of the desired compound as a colorless liquid.

EXAMPLE 28

α-8(Z)-Heptadecenyl-1,3-dioxolane-2-propanol, 35

To a solution of 0.66 g of 2-(2-bromoethyl)-1,3-dioxolane [G. Buchi and H. Wuest, J.O.C. 34, 1122 (1969)] in 5 ml of anhydrous tetrahydrofuran was added 87 mg of magnesium turnings. This mixture was stirred at 35° C. under argon for 2 hours, then cooled to −78° C. and a solution of 0.48 g of olealdehyde in 5 ml of dry tetrahydrofuran added over 5 minutes. This mixture was stirred at −78° C. for 15 minutes, then overnight at 25° C. The mixture was poured into aqueous ammonium chloride and extracted with ether. The ether extract was washed with brine, dried and evaporated to a colorless oil. Flash chromatography eluting with hexane:ethyl acetate (4:1) gave 0.47 g of the desired compound as a colorless oil.

EXAMPLE 29

4-Hydroxy-12(Z)-eicosenal-oxime, 36

A 5.0 g portion of o-8(Z)-heptadecenyl-1,3-dioxolane-2-propanol was dissolved in 200 ml of ethanol:water (3:1) and treated with 10 g of hydroxylamine hydrochloride for 12 hours. The solution was then poured into water and extracted with ether. The ether extract was washed with brine, dried and concentrated. The residual colorless oil was dissolved in 40 ml of pentane and frozen overnight, giving 3.21 g of the desired compound as a white powder.

EXAMPLE 30

1-Amino-12(Z) eicosen-4-ol, 37

A 1.5 g portion of 4-hydroxy-12(Z)-eicosenal-oxime was added to a suspension of 1.5 g of lithium aluminum hydride in ether. The mixture was stirred for 2 hours and then quenched with an excess of sodium sulfate decahydrate. Filtration and evaporation gave a white waxy solid which was crystallized from acetonitrile/ethyl acetate, giving 1.32 g of the desired compound as a white solid, mp 30° C.

EXAMPLE 31

N-(4-Hydroxy-12(Z)-eicosenyl)acetamide, 38

A 100 mg portion of 1-amino-12(Z)-eicosen-4-ol and 0.5 ml of triethylamine were dissolved in 3 ml of tetrahydrofuran. A 31 mg portion of acetic anhydride was dissolved in 3 ml of tetrahydrofuran and added dropwise over 1 minute. After stirring for 2 hours, the mixture was poured into water and extracted twice with ethyl acetate. The extracts were combined, dried and concentrated to a colorless oil which solidified upon standing Flash chromatography, eluting with dichloromethane:methanol (30:1) gave 73 mg of the desired product as a white powder, mp 50°-52° C.

EXAMPLE 32

N-(4-Oxo-12(Z)-eicosenyl)acetamide, 39

A 0.5 g portion of N-(4-hydroxy-12(Z)-eicosenyl)acetamide was stirred with 0.44 g of pyridinium chlorochromate in 15 ml of dichloromethane for 2 hours. This mixture was poured into 50 ml of ether and filtered through hydrous magnesium silicate. The filtrate was evaporated giving 0.24 g of the desired product as a pale yellow solid, mp 51°-52° C.

EXAMPLE 33

3-(Acetylamino)-N-(4-hydroxy-12(Z)-heneicosenyl)-propan amide, 40

A 400 mg portion of 1-amino-12(Z)-eicosen-4-ol and 178 mg of N-acetyl-β-alanine methyl ester were heated together at 80° C. for 18 hours under argon. The resulting waxy solid was recrystallized from methanol, giving 160 mg of the desired product as a white powder, mp 103°-108° C.

EXAMPLE 34

3-(Acetylamino)-N-(4-oxo-12(Z)-heneicosenyl)propan amide, 41

A 160 mg portion of 3-(acetylamino)-N-(4-hydroxy-12(Z)-heneicosenyl)propanamide was dissolved in 5 ml of dichloromethane and treated with 157 mg of pyridium chlorochromate for 2 hours. The solution was passed through a short pad of hydrous magnesium silicate and washed repeatedly with fresh dichloromethane. The filtrate and washes were combined and evaporated, giving 92 mg of the desired product as an off-white solid, mp 123°-125° C.

EXAMPLE 35

N-[3-[(4-Hydroxy-12(Z)-heneicosenyl)amino]-3-oxo-propyl]-2,2,5,5 tetramethyl-1,3-dioxane-4-carboxamide, 42

A 1.0 g portion of 1-amino-12(Z)-eicosen-4-ol and 0.84 g of N-[(2,2,5,5-tetramethyl-1,3-dioxan-4-yl) carbonyl]-β-alanine, methyl ester were heated together at 80° C. for 15 hours under argon. The product was flash chromatographed, eluting with dichloromethane:methanol (30:1), giving 0.9 g of the desired compound as a colorless syrup.

EXAMPLE 36

2,2,5,5-Tetramethyl-N-3-oxo-3-[(4-oxo-12(Z)-heneicosenyl) amino]propyl]-1,3-dioxane-4-carboxamide, 43

A 0.59 g portion of N-[3-[(4-hydroxy-12(Z)heneicosenyl)amino]-3-oxopropyl]-2,2,5,5-tetramethyl-1-3-dioxane-4-carboxamide was treated with pyridinium chlorochromate as described in Example 34. The product was purified by flash chromatography, eluting with dichloromethane:methanol (40:1), giving 0.44 g of the desired compound as a colorless syrup, which became a white solid on standing in the cold, mp 45°-47° C.

EXAMPLE 37

2,4-Dihydroxy-2,2-dimethyl-N-[3-oxo-3-[(4-oxo-12(Z)-heneicosenyl)amino]propyl]butanamide, 44

A 0.36 g portion of 2,2,5,5-tetramethyl-N-[3-oxo-3-[(4-oxo-12(Z)-heneicosenyl)amino]propyl]-1,3-dioxane-4-carboxamide was treated as described in Example 10. The product was purified by flash chromatography, eluting with dichloromethane:methanol (25:1), giving 0.2 g of the desired product as a milky gum.

EXAMPLE 38

2,4-Dihydroxy-N-[3-[(4-hydroxy-12(Z)-heneicosyl-)amino]-3-oxopropyl]-3,3-dimethylbutanamide, 45

A 0.89 g portion of N-[3-[(4-hydroxy-12(Z)-heneicosenyl)amino]-3-oxopropyl]-2,2,5,5-tetramethyl-1,3-dioxane-4-carboxamide was treated as described in Example 10. The crude product was purified by flash chromatography, eluting with dichloromethane:methanol (20:1), giving 0.55 g of the desired product as a colorless gum.

The compounds of this invention were tested for their ability to inhibit the acyl coenzyme A: cholesterol O-acyltransferase (ACAT) catalyzed formation of cholesterol oleate from endogenous cholesterol and exogenous $^{14}C$ oleate.

The mucosa from the Jejunum of New Zealand white rabbits was removed by scraping with a spatula and homogenized in a solution containing 0.25M sucrose, 1 mM EDTA, 1 mM dithiothreitol and 5 mM of potassium phosphate (pH 7.4). The microsomal fraction was isolated by centrifugation and stored frozen at $-70°$ C. in sucrose buffer (3 mg protein/ml) until use. The ACAT reaction was assayed using the method of S. Hashimoto, et al., Life Science 12, 1 (1973). The test compounds were dissolved in methanol at concentrations such that the addition of 0.003 ml in a reaction volume of 0.5 ml gave the final desired concentration. The results for representative compounds of this invention appear in Table I.

TABLE I

ACAT Inhibition

| Example | Compound | $IC_{50\,(uM)}$ |
|---|---|---|
| 3 | S-[2-(Acetylamino)ethyl]-9(Z)-octadecenethioic acid | >100 |
| 10 | S-[2-[[3-[(2,4-Dihydroxy-3,3-dimethyl-1-oxobutyl)amino]-1-oxopropyl]amino]ethyl]-9(Z)octadecenethioic acid | 103 |
| 6 | S-[2-[[3-(Acetylamino)-1-oxopropyl]amino]ethyl]-9(Z)-octadecenethioate | >100 |
| 11 | 2-(Acetylamino)-9(Z)-octadecenoate | >100 |
| 18 | N-[2-(Acetylamino)ethyl]-9(Z)-octadecenamide | 39 |
| 13 | 2-[[3-(Acetylamino)-1-oxopropyl]amino]ethyl-9(Z)-octadecenoate | >150 |
| 31 | N-(4-Hydroxy-12(Z)-eicosenyl)acetamide | 47 |
| 32 | N-(4-Oxo-12(Z)-eicosenyl)acetamide | 66 |
| 22 | N-[2-[[3-(Acetylamino)-1-oxopropyl]amino]ethyl]-9(Z)-octadecenamide | >100 |
| 25 | 2,2,5,5-Tetramethyl-N-[3-oxo-3-[[2-[(1-oxo-9(Z)-octadecenyl)amino]ethyl]amino]propyl]-1,3-dioxane-4-carboxamide | 1.2 |
| 17 | 2-[[3-[(2,4-Dihydroxy-3,3-dimethyl-1-oxo-butyl)amino]-1-oxopropyl]amino]ethyl-9(Z)-octadecenoate | 77 |
| 33 | 3-(Acetylamino)-N-(4-hydroxy-12(Z)-heneicosenyl)propanamide | 108 |
| 34 | 3-(Acetylamino)-N-(4-oxo-12(Z)-heneicosenyl)propanamide | 113 |
| 37 | 2,4-Dihydroxy-2,2-dimethyl-N-[3-oxo-3-[(4-oxo-12(Z)-heneicosenyl)amino]propyl]butanamide | 99 |
| 26 | N-[2-[[3-[(2,4-Dihydroxy-3,3-dimethyl-1-oxo-butyl)amino]-1-oxopropyl]amino]ethyl]-9(Z)-octadecenamide | 3.3 |
| 38 | 2,4-Dihydroxy-N-[3-[(4-hydroxy-12(Z)-heneicosyl)amino]-3-oxopropyl]-3,3-dimethylbutanamide | 57 |

Referring to the table, $IC_{50}$ indicates the concentration of the compound at which 50% of the cholesterol esterfication reaction is inhibited. The lower the $IC_{50}$ concentration the more potent the compound. As can be observed from the table, the compounds of the present invention are very potent inhibitors of the ACAT enzyme catalyzed reaction. The compounds of Example 25 and 26 are the most potent. In view of the results presented in the table, these compounds are useful for controlling and reducing the cholesteryl ester content of mammalian arterial walls and decreasing the accumulation and storage of cholesterol in the arterial walls of mammals. Further, the compounds of this invention may inhibit the formation or development of atherosclerotic lesions in mammals.

The evidence that hyperlipidemia is one of the factors involved in coronary heart disease is very impressive. A most important study carried out in Framingham, Mass. in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown to carry the highest risk of coronary heart disease. The majority of patients with ischemic heart disease or peripheral vascular disease were found to have hyperlipoproteinemia, involving very low-density and-/or low-density lipoproteins. The new compounds according to the present invention can safely and effectively lower serum lipids in warm-blooded animals. Such action on serum lipids is considered to be very useful in the treatment of atherosclerosis. For some time, it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke. While the compounds of this invention exhibit antiatherosclerotic activity, and the invention should not be construed as limited to any particular mechanism of antiatherosclerotic action.

The compounds according to the present invention have thus been shown to inhibit the ACAT catalyzed esterfication of cholesterol with fatty acids and therefore to have utility for treating atherosclerosis in mammals for reducing cholesterol content of aterial walls of mammels, for treating hyperlipidemia in mammals and for inhibiting atherosclerotic lesion development in mammals. While not wishing to be bound by any theory, it is believed that the compounds are sufficiently similar in structure to oleoyl CoA to bind to ACAT, but fail to undergo the normal acyl transfer. The compounds may thus be competitive inhibitors. Contemplated equivalents to the compounds described herein include other oleoyl CoA-like molecules in which the sissile thioester has been modified and which bind to ACAT to prevent its catalysis of the esterfication reaction.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing, for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed may vary depending on the particular compound employed, the mode of administration, and the severity of the condition being treated. In general, however, satisfactory results are obtained when the compounds of the invention are administered at a daily dosage of from about 2 mg to about 500 mg/kg of animal body weight, preferably given in divided doses two to four times a day, or in sustained release form. For most large mammals, the total daily dosage is from about 100 mg to about 5,000 mg, preferably from about 100 mg to 2,000 mg. Dosage forms suitable for internal use comprise from about 25 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose, and kaolin, while liquid carriers include sterile water, polyethylene glycols, non-ionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT, and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

We claim:

1. A compound of the formula:

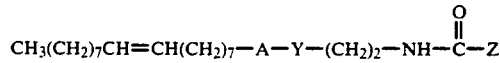

wherein A is selected from the group consisting of

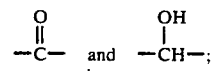

Y is —H—; and Z is

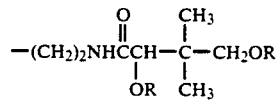

wherein R = hydrogen.

2. The compound according to claim 1, N-[2-[[3-[(2,4-dihydroxy-3,3-dimethyl-1-oxobutyl)amino]-1-oxo-propyl]amino]ethyl]-9(Z)-octadecenamide.

3. A method of treating atherosclerosis in a mammal which comprises administering to said mammal an antiatherosclerotic amount of a compound selected from those of claim 1.

4. A method of reducing the cholesterol content of the arterial wall of a mammal which comprises administering to said mammal an effective amount of a compound selected from those of claim 1.

5. A method treating hyperlipidemia in a mammal which comprises administering to said mammal an effective amount of a compound selected from those of claim 1.

6. A method of inhibiting atherosclerotic lesion development in a mammal which comprises administering to said mammal an effective amount of a compound selected from those of claim 1.

7. A composition of matter in dosage unit form comprising a compound selected from those of claim 1 in association with a pharmaceutically acceptable carrier.

* * * * *